United States Patent
Sun et al.

(10) Patent No.: US 9,480,982 B2
(45) Date of Patent: Nov. 1, 2016

(54) REACTOR FOR THE QUANTITATIVE ANALYSIS OF NUCLEIC ACIDS

(75) Inventors: Zhenhong Sun, Shanghai (CN); Wendy Wang, Shanghai (CN); Hang Liao, Shanghai (CN)

(73) Assignee: Honeywell International Inc., Morris Plains, NJ (US)

(*) Notice: Subject to any disclaimer, the term of this patent is extended or adjusted under 35 U.S.C. 154(b) by 326 days.

(21) Appl. No.: 12/810,151

(22) PCT Filed: Dec. 24, 2007

(86) PCT No.: PCT/CN2007/003755
§ 371 (c)(1),
(2), (4) Date: Sep. 15, 2010

(87) PCT Pub. No.: WO2009/079857
PCT Pub. Date: Jul. 2, 2009

(65) Prior Publication Data
US 2011/0020818 A1    Jan. 27, 2011

(51) Int. Cl.
*C12Q 1/68* (2006.01)
*B01L 3/00* (2006.01)
*B01L 7/00* (2006.01)

(52) U.S. Cl.
CPC ............. *B01L 3/508* (2013.01); *B01L 3/5027* (2013.01); *B01L 3/50851* (2013.01); *B01L 3/502715* (2013.01); *B01L 7/52* (2013.01); *B01L 2200/027* (2013.01); *B01L 2200/0689* (2013.01); *B01L 2300/0636* (2013.01); *B01L 2300/0822* (2013.01)

(58) Field of Classification Search
None
See application file for complete search history.

(56) References Cited

U.S. PATENT DOCUMENTS

| | | | |
|---|---|---|---|
| 4,115,356 A * | 9/1978 | Hilliard | 528/18 |
| 4,683,195 A | 7/1987 | Mullis et al. | |
| 4,683,202 A | 7/1987 | Mullis | |
| 4,965,188 A | 10/1990 | Mullis et al. | |
| 5,461,134 A | 10/1995 | Leir et al. | |
| 5,750,337 A * | 5/1998 | Squirrell | C12Q 1/6825 422/50 |
| 5,830,645 A | 11/1998 | Pinkel et al. | |
| 6,007,914 A | 12/1999 | Joseph et al. | |
| 7,384,782 B2 * | 6/2008 | Nakatani et al. | 435/288.1 |
| 7,790,441 B2 | 9/2010 | Nakatani et al. | |
| 2001/0005718 A1 | 6/2001 | Wen-Tung et al. | |

(Continued)

FOREIGN PATENT DOCUMENTS

| CN | 1368555 A | 9/2002 |
|---|---|---|
| CN | 1526827 A | 9/2004 |

(Continued)

OTHER PUBLICATIONS

Erickson et al. (Lap Chip 2003, vol. 3, p. 141-149).*

(Continued)

*Primary Examiner* — Stephanie K Mummert
(74) *Attorney, Agent, or Firm* — Schwegman Lundberg & Woessner, P.A.

(57) ABSTRACT

A reactor for the quantitative analysis of target nucleic acids using an evanescent wave detection technique and a method of use thereof is provided. The reactor includes a substrate with a cavity, a buffer layer arranged over the substrate; a cover plate arranged over the buffer layer, and inlet and outlet ports. The reactor is thermally and chemically stable for PCR processing and suitable for an evanescent wave detection technique.

6 Claims, 2 Drawing Sheets

(56) References Cited

U.S. PATENT DOCUMENTS

| | | | |
|---|---|---|---|
| 2002/0164629 | A1 | 11/2002 | Quake et al. |
| 2003/0186228 | A1 | 10/2003 | McDevitt et al. |
| 2004/0106130 | A1 | 6/2004 | Besemer et al. |
| 2004/0112529 | A1 | 6/2004 | Karlsson et al. |
| 2006/0088844 | A1 | 4/2006 | Xu |
| 2006/0160097 | A1* | 7/2006 | Nakatani et al. ............... 435/6 |
| 2007/0042367 | A1* | 2/2007 | Tao et al. ....................... 435/6 |
| 2007/0154922 | A1 | 7/2007 | Collier et al. |
| 2009/0169427 | A1 | 7/2009 | Supriya et al. |
| 2009/0227474 | A1 | 9/2009 | Gordon et al. |
| 2013/0040295 | A1 | 2/2013 | Sun et al. |

FOREIGN PATENT DOCUMENTS

| | | |
|---|---|---|
| CN | 1537165 A | 10/2004 |
| CN | 1637147 A | 7/2005 |
| CN | 1981188 A | 6/2007 |
| CN | 102791882 A | 11/2012 |
| EP | 1935496 A1 | 6/2008 |
| IN | 6384DELNP2012 A | 10/2015 |
| WO | WO-96/34028 A1 | 10/1996 |
| WO | WO-96/34029 A1 | 10/1996 |
| WO | WO-96/35458 A2 | 11/1996 |
| WO | WO-99/13110 A1 | 3/1999 |
| WO | WO-00/68336 A1 | 11/2000 |
| WO | WO-01/32930 A1 | 5/2001 |
| WO | WO-01/37958 A2 | 5/2001 |
| WO | WO-2005/094981 A1 | 10/2005 |
| WO | WO-2005/108604 A2 | 11/2005 |
| WO | WO-2009/059447 A1 | 5/2009 |
| WO | WO-2009/079857 A1 | 7/2009 |
| WO | WO-2011/088588 A1 | 7/2011 |

OTHER PUBLICATIONS

Stimpson et al. (Nucleic Acids Research, 1995, vol. 92, p. 6379-6383).*
Hofmann et al. (Lab Chip, 2001, vol. 1, p. 108-114).*
Jalali et al. (IEEE Journal of Selected Topics in Quantum Electronics; 1998, 4(6):938-947).*
Zhou et al. (Proceedings of SPIE, 2001, vol. 4470, p. 138-145).*
"International Application Serial No. PCT/CN2010/000083, International Search Report mailed Nov. 4, 2010", 5 pgs.
"International Application Serial No. PCT/US2007/003755, International Search Report mailed Sep. 18, 2008", 4 pgs.
"International Application Serial No. PCT/US2007/003755, Written Opinion mailed Sep. 18, 2008", 4 pgs.
"Chinese Application Serial No. 200780102406.9, Office Action mailed Aug. 29, 2012", 24 pgs.
"Chinese Application Serial No. 200780102406.9, Office Action Response filed Feb. 16, 2013", 9 pgs.
"Chinese Application Serial No. 200780102406.9, Office Action mailed Jun. 25, 2013", (w/ English Translation), 27 pgs.
"International Application Serial No. PCT/CN2010/000083, International Preliminary Report on Patentability dated Jul. 24, 2012", 6 pgs.
"International Application Serial No. PCT/CN2010/000083, Written Opinion mailed Nov. 4, 2010", 5 pgs.
"International Application Serial No. PCT/US2007/003755, International Preliminary Report on Patentability dated Aug. 19, 2008", 9 pgs.
Tao, Guoliang, et al., "Research on Graphite/Polypropylene/Carbon Fibre Composites with High Strength and Heat Conductivity", (w/ English Abstract), China Plastics, vol. 18 (11), (2004), 32-35.
"Chinese Application Serial No. 200780102406.9, Response filed May 28, 2014 to Office Action mailed Mar. 13, 2014", (w/ English Translation of Amended Claims), 13 pgs.
"U.S. Appl. No. 13/522,938, Response filed Jul. 10, 2014 to Non Final Office Action mailed Mar. 13, 2014", 20 pgs.
"Chinese Application Serial No. 201080065414.2, Office Action mailed May 20, 2014", (w/ English Translation), 21 pgs.
"Chinese Application Serial No. 200780102406.9, Response filed Nov. 11, 2013 to Office Action mailed Jun. 25, 2013", (w/ English Translation), 10 pgs.
"Chinese Application Serial No. 201080065414.2, Office Action mailed Aug. 30, 2013", (w/ English Translation), 12 pgs.
"U.S. Appl. No. 13/522,938, Non Final Office Action mailed Mar. 13, 2014", 28 pgs.
"U.S. Appl. No. 13/522,938, Response filed Feb. 12, 2014 to Restriction Requirement mailed Jan. 14, 2014", 6 pgs.
"U.S. Appl. No. 13/522,938, Restriction Requirement mailed Jan. 14, 2014", 8 pgs.
"Chinese Application Serial No. 20078012406.9, Office Action mailed Mar. 13, 2014", (w/ English Translation), 21 pgs.
"Chinese Application Serial No. 201080065414.2, Respones filed Jan. 13, 2014 to Office Action mailed Aug. 30, 2013", (English Translation of Amended Claims), 5 pgs.
"Cool Polymers", CoolPoly® D1202 Thermally Conductive Polypropylene (PP) Preliminary Product Datasheet, (2007), 1 pg.
"Dow Corning", Dow Corning® 3145 RTV MIL-A-46146 Adhesive/Sealant-Clear Material Safety Data Sheet, (2013), 9 pgs.
"European Application Serial No. 07855763.4, Extended European Search Report mailed Apr. 7, 2014", 4 pgs.
Dahl, Andreas, et al., "Quantitative PCR based expression analysis on a nanoliter scale using polymer nano-well chips", Biomedical Microdevices, 9(3), (2007), 307-314.
Festag, Grit, et al., "Optimization of gold nanoparticle-based DNA detection for microarrays", Journal of Fluorescence, 15(2), (2005), 161-170.
Northrup, M. Allen, et al., "A miniature Analytical Instrument for Nucleic Acids Based on micromachined silicon reaction chambers", Analytical Chemistry, 70(5), (1998), 918-922.
Taylor, Scott, et al., "Impact of surface chemistry and blocking strategies on DNA microarrays", Nucleic Acids Research, 31(16): e87, (2003), 1-19.
"European Application Serial No. 07855763.4, Response filed Apr. 20, 2015 to Office Action mailed Oct. 14, 2014", 9 pgs.
"U.S. Appl. No. 13/522,938, Final Office Action mailed Nov. 6, 2014", 37 pgs.
"U.S. Appl. No. 13/522,938, Preliminary Amendment filed Jul. 18, 2012", 7 pgs.
"U.S. Appl. No. 13/522,938, Response filed Jan. 15, 2015 to Final Office Action mailed Nov. 6, 2014", 15 pgs.
"Chinese Application Serial No. 201080065414.2, Response filed Oct. 8, 2014 to Office Action mailed May 20, 2014", (w/ English Translation of Amended Claims), 9 pgs.
"European Application Serial No. 07855763.4, Office Action mailed Oct. 14, 2014", 10 pgs.
"U.S. Appl. No. 13/522,938, Non Final Office Action mailed Sep. 4, 2015", 19 pgs.
Okahata, Yoshio, et al., "Hybridization of Nucleic Acids Immobilized on a Quartz Crystal Microbalance", J. Am. Chem. Soc., 114(21), (1992), 8299-8300.
"Application Serial No. 13/522, Response filed Dec. 2, 2015 to Non Final Office Action mailed Sep. 4, 2015", 14 pgs.
"U.S. Appl. No. 13/522,938, Non Final Office Action mailed Jan. 12, 2016", 7 pgs.
"Chinese Application Serial No. 201080065414.2, Decision mailed Dec. 31, 2014", (w/English Translation), 18 pgs.

* cited by examiner

REACTOR FOR THE QUANTITATIVE ANALYSIS OF NUCLEIC ACIDS

BACKGROUND OF THE INVENTION

An important technique currently used in bioanalysis and in the emerging field of genomics is the polymerase chain reaction (PCR) amplification of DNA. As a result of this powerful tool, it is possible to start with otherwise undetectable amounts of DNA and create ample amounts of the material for subsequent analysis. PCR uses a repetitive series of steps to create copies of polynucleotide sequences located between two initiating ("primer") sequences. Starting with a template, two primer sequences (usually about 15-30 nucleotides in length), PCR buffer, free deoxynucleoside tri-phosphates (dNTPs), and thermostable DNA polymerase (commonly TAQ polymerase from *Thermus aquaticus*), these components are mixed, and heated to separate the double-stranded DNA. A subsequent cooling step allows the primers to anneal to complementary sequences on single-stranded DNA molecules containing the sequence to be amplified. Replication of the target sequence is accomplished by the DNA polymerase, which produces a strand of DNA that is complementary to the template. Repetition of this process doubles the number of copies of the sequence of interest, and multiple cycles increase the number of copies exponentially.

Since PCR requires repeated cycling between higher and lower temperatures, PCR devices must be fabricated from materials capable of withstanding such temperature changes. The materials must be mechanically and chemically stable at high temperatures, and capable of withstanding repeated temperature changes without mechanical degradation. Furthermore, the materials must be compatible with the PCR reaction itself, and not inhibit the polymerase or bind DNA.

Conventional PCR is typically carried out in tubes, microplates, and capillaries, all of which could be sealed conveniently. However, the geometry of these tubes, microplates, and capillaries render them not suitable for evanescent wave detection methods.

BRIEF DESCRIPTION OF THE DRAWINGS

Embodiments of the invention may be best understood by referring to the following description and accompanying drawings, which illustrate such embodiments. In the drawings.

DEFINITIONS

Figure 1:
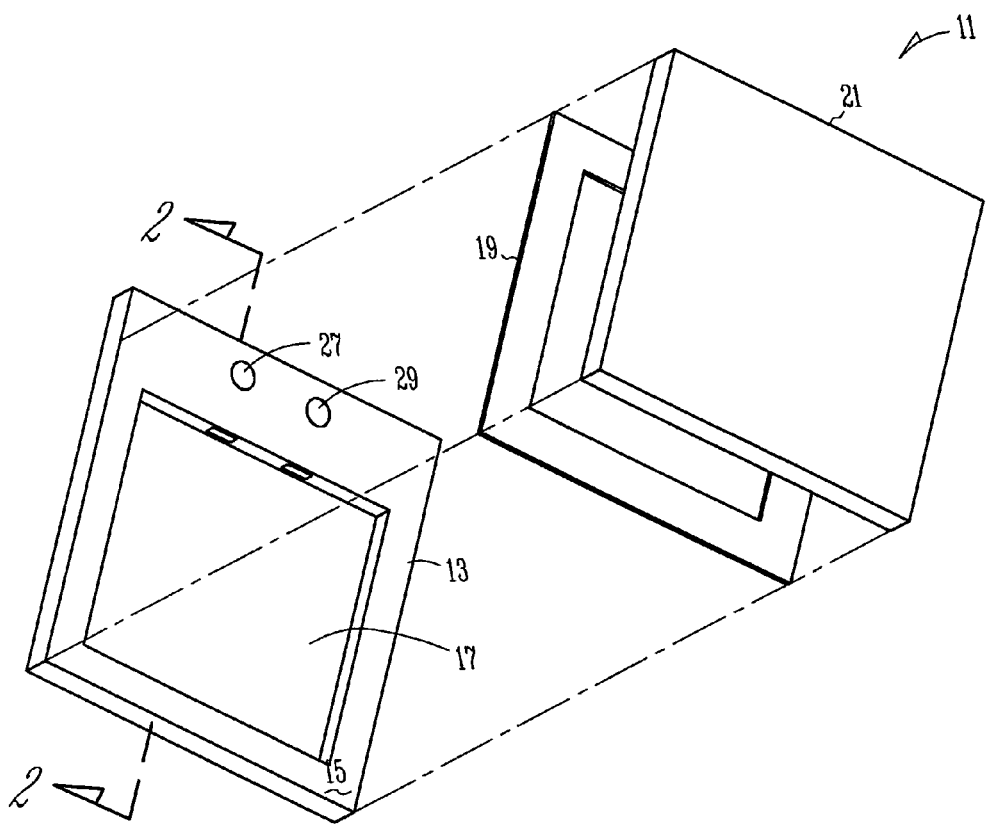
FIG. 1 illustrates a view of a cartridge capable of evanescent wave detection of fluorescently tagged amplicons in a microarrayed PCR process.

As used herein, certain terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 11th Edition, by Sax and Lewis, Van Nostrand Reinhold, New York, N.Y., 1987, and *The Merck Index*, 11th Edition, Merck & Co., Rahway N.J. 1989.

As used herein, the term "and/or" means any one of the items, any combination of the items, or all of the items with which this term is associated.

As used herein, the singular forms "a," "an," and "the" include plural reference unless the context clearly dictates otherwise. Therefore, for example, a reference to "a formulation" includes a plurality of such formulations, so that a formulation of compound X includes formulations of compound X.

As used herein, the term "about" means a variation of 10 percent of the value specified, for example, about 50 percent carries a variation from 45 to 55 percent. For integer ranges, the term about can include one or two integers greater than and less than a recited integer.

As used herein, the term "amplicons" refers to the products of polymerase chain reactions (PCR). Amplicons are pieces of DNA that have been synthesized using amplification techniques (e.g., a double-stranded DNA with two primers). The amplicon may contain, for example, a primer tagged with a fluorescent molecule at the 5' end.

As used herein, the terms "array" and "microarray" refer to an arrangement of elements (i.e., entities) into a material or device. In another sense, the term "array" refers to the orderly arrangement (e.g., rows and columns) of two or more assay regions on a substrate.

As used herein, the term "evanescent" refers to a nearfield standing wave exhibiting exponential decay with distance. As used in optics, evanescent waves are formed when sinusoidal waves are internally reflected off an interface at an angle greater than the critical angle so that total internal reflection occurs.

As used herein, the term "hybridization" refers to the pairing of complementary nucleic acids.

As used herein, the term "motive force" is used to refer to any means for inducing movement of a sample along a flow path in a reactor, and includes application of an electric potential across any portion of the reactor, application of a pressure differential across any portion of the reactor or any combination thereof.

As used herein, the term "nucleic acid molecule" refers to any nucleic acid containing molecule including, but not limited to, DNA or RNA.

As used herein, the term "optical detection path" refers to a configuration or arrangement of detection means to form a path whereby electromagnetic radiation is able to travel from an external source to a means for receiving radiation, wherein the radiation traverses the reaction chamber.

As used herein, the term "polymerase chain reaction" (PCR) refers to the method of K. B. Mullis, U.S. Pat. Nos. 4,683,195, 4,683,202, and 4,965,188.

As used herein, the term "reactor" refers to a device, which can be used in any number of chemical processes involving a fluid. The primary process of interest is the amplification of DNA using the polymerase chain reaction. Optionally, DNA amplification may be conducted along with one or more other types of procedures.

As used herein, the term "stability" refers to the ability of a material to withstand deterioration or displacement and to provide reliability and dependability.

As used herein, the term "substrate" refers to material capable of supporting associated assay components (e.g., assay regions, cells, test compounds, etc.).

As used herein, the term "target nucleic acid" refers to a polynucleotide inherent to a pathogen that is to be detected.

The polynucleotide is genetic material including, for example, DNA/RNA, mitochondrial DNA, rRNA, tRNA, mRNA, viral RNA, and plasmid DNA.

As used herein, the term "water impermeable" refers to a material in which water will not pass through the material.

DETAILED DESCRIPTION OF THE INVENTION

The present invention provides a reactor for the quantitative analysis of target nucleic acids using an evanescent wave detection technique and a method of use thereof. The reactor includes a substrate with a cavity, a buffer layer arranged over the substrate; a cover plate arranged over the buffer layer, and inlet and outlet ports. The reactor is thermally and chemically stable for PCR processing and suitable for an evanescent wave detection technique.

The PCR process that occur inside the reactor require special temperature conditions, such as a circular cycle of high and low temperatures. The temperature change of the liquid and the reaction chamber are regulated by a heating and cooling system.

At high temperatures, the sample liquid expands and increases the pressure inside the reaction chamber. Conversely, at low temperatures, the sample liquid shrinks and decreases the pressure inside the reaction chamber. Any deformation of the reaction chamber will cause incomplete adherence between the cover layer and the substrate and result in leakage. In the case of PCR amplification, even a small amount of little leakage may result in false positives. To prevent this leakage, a buffer layer is used.

For real-time quantitative analysis of target nucleic acids, several methods utilizing evanescent wave detection techniques have been disclosed including, for example, the techniques described in Xu (U.S. Patent Application Publication No. 2006/0088844) and in PCT Patent Application Serial No. PCT/CN2007/003124, entitled "A QUANTITATIVE METHOD FOR OLIGONUCLEOTIDE MICROARRAY" filed Nov. 5, 2007.

In these methods describing the real-time quantitative analysis of target nucleic acids, the target nucleic acids in the sample are amplified using the polymerase chain reaction (PCR). PCR is begun by placing the target nucleic acids in a buffer containing the nucleotides adenine (A), thymine (T), cytosine (C) and guanine (G) (collectively referred to as dNTPs), a DNA polymerase, and primers. The primers are short strands of DNA, with sequences that complement specific regions of the target nucleic acids. The primers initiate replication of the target nucleic acids. The primers may be fluorescently tagged with fluorescent molecules at the 5' end or the dNTPs are fluorescently tagged.

This type of PCR process has three main steps: denaturation, annealing and extension. In the denaturation step, the mixture is heated to about 94° C. (Centigrade), at which point the target DNA separates into single strands. The mixture is quickly cooled. As the temperature falls to about 60° C., the annealing step occurs, in which the primers, which are fluorescently tagged, hybridize or bind to their complementary sequences on the target nucleic acids. The extension step may be performed at about 60° C. or may be raised to the 72-78° C. range. In this step, the DNA polymerase uses the dNTPs in solution to extend the annealed primers, which are fluorescently tagged, and forms new strands of DNA known as amplicons. The mixture is briefly reheated back to about 94° C. to separate the newly created double helix stands into single strands of nucleic acid, which begins another cycle of the PCR process. With each cycle of the PCR process, the number of copies of the original target nucleic acids roughly doubles.

The PCR buffer may additionally contain fluorescently tagged primers, that is, primers having a fluorescent dye molecule attached to them, so that upon completion of each PCR cycle, the amplicons produced are fluorescently tagged. The amplicons of the target nucleic acids are localized, using probe strands of DNA known as target nucleic acid probes. The target nucleic acid probes have the same complementary, nucleotide sequence as the target nucleic acids. The target nucleic acid probes are tethered to a substrate surface in a known, two-dimensional pattern, with the substrate surface forming part of the reaction cell containing the PCR ingredients.

The PCR buffer may also include coating agents or surfactants to prevent nonspecific binding by modifying the interior surfaces of the reactor. Examples of such coating agents include polyethylene oxide triblock copolymers, polyethylene glycols (PEG) having molecular weights ranging from about 200 to about 8000, natural polymers such as bovine serum albumen (BSA) or any other moieties that provide the desired surface characteristics, particularly those that reduce the sorption of biomolecules such as proteins and nucleic acid A solution containing the sample to be amplified and appropriate buffers and reagents is typically introduced into the reactor via any appropriate methodology. Introduction of the sample may be achieved using any convenient means, including electrokinetic injection, hydrodynamic injection, spontaneous fluid displacement and the like. The particular means employed will, for the most part, depend on the configuration of the channel as well as the necessity to introduce a precise volume of sample.

During the annealing and extension phases of the PCR process, the target amplicons hybridize to their corresponding target nucleic acid probes. The hybridized, fluorescently tagged amplicons are illuminated with an evanescent wave of light of the appropriate wavelength to activate the fluorescent dye molecules of the fluorescently tagged primers or the fluorescently tagged dNTPs. This evanescent wave decays exponentially in power after entering the reaction cell via the substrate surface to which the target nucleic acid probes are tethered, with an effective penetration range of about 300 nm. This means that the evanescent wave penetrates far enough into the reaction cell to activate the fluorescently tagged amplicons hybridized to those target nucleic acid probes, but that it does not activate the fluorescently tagged molecules (e.g., the fluorescently tagged primers or the fluorescently tagged dNTPs) in solution in the main body of the reaction cell. By monitoring the strength of the fluorescence at various locations on the substrate surface, the current abundance of amplicons of the corresponding target nucleic acids can be determined. The results are used to obtain a quantitative measure of the abundance of a specific target in the original sample, in a manner analogous to the real-time PCR calculation.

The Reactor

In an embodiment, FIG. 1 schematically illustrates a reactor that can be used in conducting a chemical process such as PCR. The device is generally represented at 11, comprising substrate 13 having a planar surface 15 and containing a cavity 17. A buffer layer 19 is shown arranged over the planar surface 15 of substrate 13. A cover plate 21 is shown arranged over the top surface 23 of the buffer layer 19.

Figure 2:
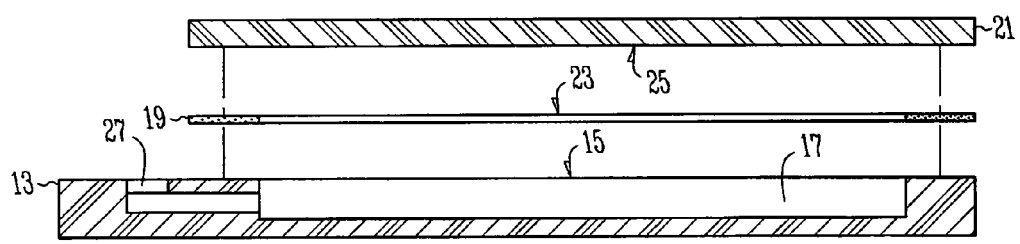
FIG. 2 illustrates a side view of a cartridge capable of evanescent wave detection of fluorescently tagged amplicons in a microarrayed PCR process.

Prior to use of the device, the underside 25 of the cover plate 21 is aligned with and placed against the top surface 23 of the buffer layer 19 on the planar surface 15 of substrate 13 (see, e.g., FIG. 2). The cover plate 21, in combination with the buffer layer 19, and cavity 17, form a reaction chamber in which the desired chemical process is carried out. Fluid, e.g., sample to be analyzed, analytical reagents, reactants or the like, are introduced into the reaction chamber from an external source through inlet port 27. The outlet port 29 enables passage of fluid from the reaction chamber to an external receptacle. Accordingly, the reactor is closed by aligning the cover plate 21 with the buffer layer 19 on substrate 13, forming a seal. In some embodiments, the buffer layer 19 is not cured. In other embodiments, the buffer layer 19 is cured. This seal results in formation of a reaction chamber into which fluids may be introduced through inlet port 27 and removed through outlet port 29. A set of plugs (e.g., rubber) with the proper size, hardness, and chemical resistance may be used to seal the inlet port 27 and outlet port 29 of the reaction chamber.

Figure 3:
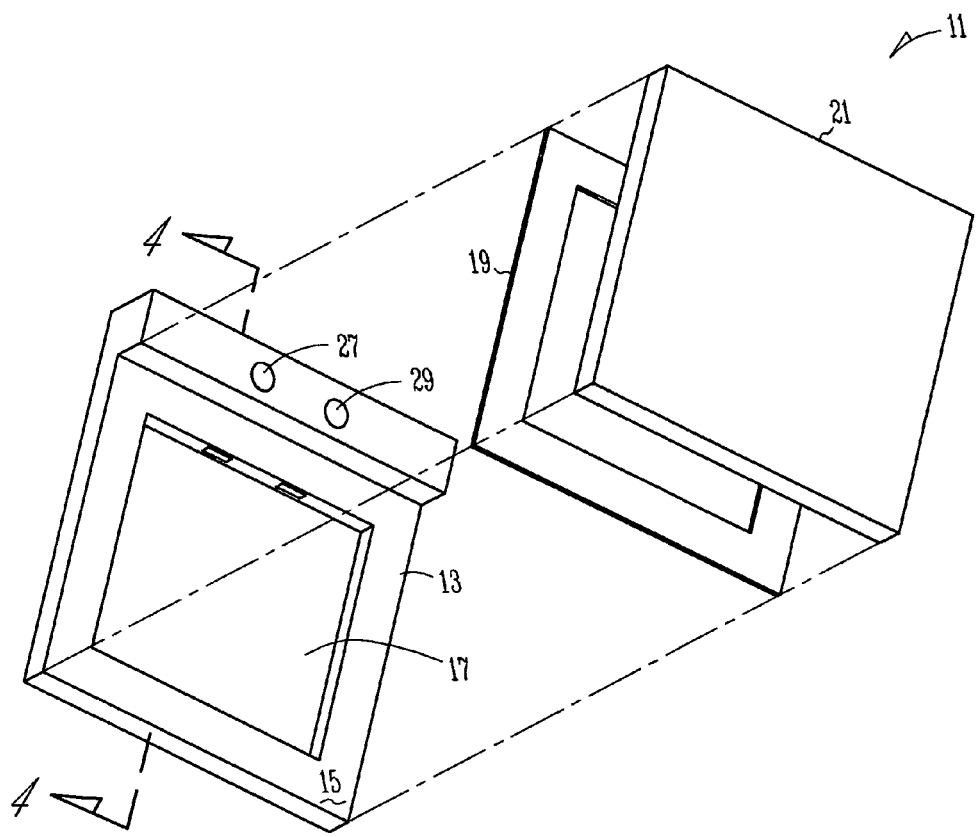
FIG. 3 illustrates a view of another cartridge capable of evanescent wave detection of fluorescently tagged amplicons in a microarrayed PCR process.

In another embodiment, FIG. 3 schematically illustrates a reactor that can be used in conducting a chemical process such as PCR. The device is generally represented at 11, comprising substrate 13 having a planar surface 15 and containing a cavity 17. A buffer layer 19 is shown arranged over the planar surface 15 of substrate 13. A cover plate 21 is shown arranged over the top surface 23 of the buffer layer 19.

Figure 4:
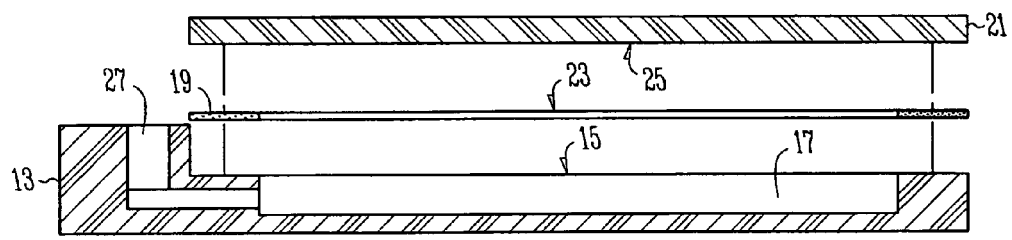
FIG. 4 illustrates a side view of another cartridge capable of evanescent wave detection of fluorescently tagged amplicons in a microarrayed PCR process.

Prior to use of the device, the underside 25 of the cover plate 21 is aligned with and placed against the top surface 23 of the buffer layer 19 on the planar surface 15 of substrate 13 (see, e.g., FIG. 4). The cover plate 21, in combination with the buffer layer 19, and cavity 17, form a reaction chamber in which the desired chemical process is carried out. Fluid, e.g., sample to be analyzed, analytical reagents, reactants or the like, are introduced into the reaction chamber from an external source through inlet port 27. The outlet port 29 enables passage of fluid from the reaction chamber to an external receptacle. Accordingly, the reactor is closed by aligning the cover plate 21 with the buffer layer 19 on substrate 13, forming a seal. In some embodiments, the buffer layer 19 is not cured. In other embodiments, the buffer layer 19 is cured. This seal results in formation of a reaction chamber into which fluids may be introduced through inlet port 27 and removed through outlet port 29. A set of plugs (e.g., rubber) with the proper size, hardness, and chemical resistance may be used to seal the inlet port 27 and outlet port 29 of the reaction chamber.

The Substrate and Cover Plate

The materials used to form the substrates and cover plates in the embodiments are selected with regard to physical and chemical characteristics that are desirable for a particular application. The substrate and cover plates should be chemically inert and physically stable with respect to any reagents with which they comes into contact, under the reaction conditions used (e.g., with respect to pH, electric fields, etc.). Since PCR involves relatively high temperatures, it is important that all materials be chemically and physically stable within the range of temperatures used. For use with optical detection means, the materials used should be optically transparent, typically transparent to wavelengths in the range of about 150 nm to 800 nm.

For example, in some embodiments, the substrate includes a planar (i.e., 2 dimensional) glass, metal, composite, plastic, silica, or other biocompatible or biologically unreactive composition. Many substrates may be employed. The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate is generally flat but may take on a variety of alternative surface configurations. For example, the substrate may contain raised or depressed regions on which the synthesis takes place. The substrate and its surface can form a rigid support on which to carry out the reactions described herein. The substrate and its surface are also chosen to provide appropriate light-absorbing characteristics. For instance, the substrate may be a polymerized Langmuir Blodgett film, a glass, a functionalized glass, Si, Ge, GaAs, GaP, $SiO_2$, $SiN_4$, modified silicon, or any one of a wide variety of gels or polymers, for example, (poly)tetrafluoroethylene, (poly)vinylidenedifluoride, polystyrene, polycarbonate, or combinations thereof.

Suitable materials for forming the present reactors include, but are not limited to, polymeric materials, ceramics (including aluminum oxide and the like), glass, quartz, metals, composites, and laminates thereof.

In one embodiment, the substrate is glass. In other embodiments, the substrate is a polymeric material.

Polymeric materials will typically be organic polymers that are homopolymers or copolymers, naturally occurring or synthetic, crosslinked or uncrosslinked. Specific polymers of interest include, but are not limited to, polyolefins such as polypropylene, polyimides, polycarbonates, polyesters, polyamides, polyethers, polyurethanes, polyfluorocarbons, polystyrenes, poly(acrylonitrile-butadiene-styrene) (ABS), acrylate and acrylic acid polymers such as polymethyl methacrylate, and other substituted and unsubstituted polyolefins, and copolymers thereof.

The substrate and the cover plate may also be fabricated from a "composite," i.e., a composition comprised of unlike materials. The composite may be a block composite, e.g., an A-B-A block composite, an A-B-C block composite, or the like. Alternatively, the composite may be a heterogeneous combination of materials, i.e., in which the materials are distinct from separate phases, or a homogeneous combination of unlike materials. As used herein, the term "composite" is used to include a "laminate" composite. As used herein, the term "laminate" refers to a composite material formed from several different bonded layers of identical or different materials. Other composite substrates include polymer laminates, polymer-metal laminates, e.g., polymer coated with copper, a ceramic-in-metal, or a polymer-in-metal composite.

The surfaces of the substrates and cover plates may be chemically modified to provide desirable chemical or physical properties, e.g., to reduce adsorption of molecular moieties to the interior walls of a reaction chamber, and to reduce electro osmotic flow. For example, the surface of a glass, a polymeric, or a ceramic substrate and/or cover plate may be coated with or functionalized to contain electrically neutral molecular species, zwitterrionic groups, hydrophilic or hydrophobic oligomers or polymers, etc. With polyimides, polyamides, and polyolefins having reactive sites or functional groups such as carboxyl, hydroxyl, amino and haloalkyl groups (e.g., polyvinyl alcohol, polyhydroxystyrene, polyacrylic acid, polyacrylonitrile, etc.), or with polymers that can be modified so as to contain such reactive sites or functional groups, it is possible to chemically bond groups to the surface that can provide a variety of desirable surface properties. A modified substrate is polyimide functionalized so as to contain surface-bound water-soluble polymers such as polyethylene oxide (PEO), which tends to reduce unwanted adsorption and minimize nonspecific binding in DNA amplification and other methodologies involving hybridization techniques. The substrate surface may also be advantageously modified using surfactants (e.g., polyethylene oxide triblock copolymers such as those available under the tradename "Pluronic," polyoxyethylene sorbitan, or "TWEEN"), natural polymers (e.g., bovine serum albumin or "BSA"), or other moieties that provide the desired surface characteristics, particularly in reducing the sorption of biomolecules such as nucleic acids or proteins.

It should also be emphasized that different regions of a single substrate may have chemically different surfaces. For example, the reaction chamber may have one interior surface that is coated or functionalized, e.g., with polyethylene oxide or the like, while another interior surface of the reaction chamber may not be coated or functionalized. In this way, different components and features present in the same substrate may be used to conduct different chemical or biochemical processes, or different steps within a single chemical or biochemical process.

The substrate may be a thermally conductive material with a thermal conductivity greater than about 0.1 W/mK, or greater than about 0.5 W/mK, or greater than about 1 W/mK. This allows for fast heat transfer during the rapid heating and cooling cycles.

In one embodiment, the substrate is a thermally conductive polypropylene with a thermal conductivity greater than about 1 W/mK. Thermally conductive polypropylenes typically include materials that act as heating elements. Suitable heat conducting materials may include, for example, iron, nickel, cobalt, chromium; carbon steel fibers, magnetic stainless steel fibers, nickel fibers, ferromagnetic coated electrically conductive fibers, ferromagnetic coated electrically nonconductive fibers, and alloys thereof.

In one embodiment, the substrate is heated to raise the temperature of the reactor. In another embodiment, the substrate is cooled to lower the temperature of the reactor. In yet another embodiment, the substrate is both heated and then cooled to regulate the temperature of the reactor.

In one embodiment, the cover plate is glass.

The Buffer Layer

In the reactor, a buffer layer is used between the substrate and the cover plate. The buffer layer should have good adhesion to the substrate and the cover plate. The buffer layer should also be impenetrable by the liquid used in the sample. The buffer layer should be able to withstand repeated cycling between 4° C. through 95° C. for extended periods of time (e.g., 1-2 hours). The buffer layer should also not interfere with the PCR process and the detection system.

A variety of buffer layers may be used, although any buffer layer selected should be capable of withstanding the forces generated during processing of any sample materials located in the reaction chamber, for example, forces developed during distribution of the sample materials, forces developed during thermal processing of the sample materials, etc. Those forces may be large where, for example, the processing involves thermal cycling. In one embodiment, the buffer layer used in connection with the sample processing devices should exhibit low fluorescence and be compatible with the processes and materials to be used in connection with PCR.

In one embodiment, the buffer layer may exhibit sealant and/or adhesive properties. Such buffer layers may be more amenable to high volume production of sample processing devices since they typically do not involve the high temperature bonding processes used in melt bonding, nor do they present the handling problems inherent in use of liquid adhesives, solvent bonding, ultrasonic bonding, and the like.

In one embodiment, the buffer layer may include materials which ensure that the properties of the buffer layer are not adversely affected by water. For example, the buffer layer should not lose adhesion, lose cohesive strength, soften, swell, or opacify in response to exposure to water during sample loading and processing. Also, the buffer layer should not contain any components which may be extracted into water during sample processing, thus possibly compromising the device performance.

Furthermore, the buffer layer can be a single material or a combination or blend of two or more materials. The buffer layer may result from, for example, solvent coating, screen printing, roller printing, melt extrusion coating, melt spraying, stripe coating, or laminating processes. A buffer layer can have a wide variety of thicknesses as long as it meets exhibits the above characteristics and properties. In order to achieve maximum bond fidelity and, if desired, to serve as a passivating layer, the buffer layer should be continuous and free from pinholes or porosity.

Any adhesive composition known in the art can be applied as the buffer layer. Suitable adhesive compositions are described in, for example, "Adhesion and Bonding," Encyclopedia of Polymer Science and Engineering, Vol. 1, pp. 476-546, Interscience Publishers, Second Ed., 1985. In one embodiment, the adhesive compositions are water-impermeable. Suitable water impermeable adhesives include, for example, natural rubber latex based adhesives, synthetic rubber based adhesives, silicon based adhesives, and hot-melt adhesives. Many other adhesives can also be used for purposes of the present invention the particular choice being dependent on the character of the two surfaces to be bound to each other, the circumstances under which the bonding is to be accomplished and the intended use of the resulting products. A thorough discussion of adhesives can be found in Ullmann's Encyclopedia of Industrial Chemistry, VCH Verlagsgesellschaft GmbH, Germany, 1985, Vol. A1, at pages 221-267 and Encyclopedia of Chemical Technology, Fourth Ed., John Wiley & Sons, NYC, 1991, Vol. 1, at pages 445-466. Curable adhesives are also be used. However, contact, pressure sensitive, rubber based, emulsion, hot melt, natural product, polyurethane, acrylic, epoxy, phenolic, and polyimide adhesives may also be used.

Suitable classes of sealant compositions may also include, for example, polyurethanes, polyisobutylenes, butyl rubbers, elastomers, epoxys, natural and synthetic rubber, silicones, polysulfides, acrylates, and combinations thereof. Sealant compositions may include polar and/or reactive groups (e.g., silane, urethane, ester, mercapto, and combinations thereof) to provide sufficient covalent, and/or polar (e.g., hydrogen) bonding with the target substrates (e.g., glass and plastic).

In one embodiment, the buffer layer may be composed of hydrophobic materials. In one embodiment, the buffer layer may be composed of silicone materials.

In one embodiment, a silicon sealant is used. Silicone sealants typically include a mixture of a silicone polymer, one or more fillers, a crosslinking component such as a reactive silane, and a catalyst. The silicone polymer has a siloxane backbone and includes pendant alkyl, alkoxy, or acetoxy groups. Such groups are hydrolyzed to silanol groups which form larger chains by condensation. The silicone sealants may be applied by means of a caulking gun, a spatula, or other suitable method and are cured by exposure in moist air. The silicone sealants have low shrinkage characteristics and may be applied and used over a wide temperature range. Room Temperature Vulcanizing (RTV) silicone rubber sealants are particularly useful due to their mild curing conditions. Suitable Room Temperature Vulcanizing (RTV) silicone rubber sealants include, for example, a one component RTV rubber (KE3475, Shin-Etsu Chemical Co., Ltd., Japan) and the one-part moisture cure RTV (SE 9120, Dow Corning Corporation, Midland, Mich., USA).

In addition to moisture curing silicon sealant materials, radiation-curable silicon sealants may also be used. A suitable ultraviolet radiation-curable silicone sealant composition typically comprises (i) an organopolysiloxane containing radiation-sensitive functional groups and (ii) a photoinitiator. Examples of radiation-sensitive functional groups include acryloyl, methacryloyl, mercapto, epoxy, and alkenyl ether groups. The type of photoinitiator depends on the nature of the radiation-sensitive groups in the organopolysiloxane. Examples of photoinitiators may include diaryliodonium salts, sulfonium salts, acetophenone, benzophenone, and benzoin and its derivatives. A particularly useful type of unsaturated organosilicon compound has at least one aliphatically unsaturated organic radical attached to silicon per molecule. The aliphatically unsaturated organosilicon compounds include silanes, polysilanes, siloxanes, silazanes, as well as monomeric or polymeric materials containing silicon atoms joined together by methylene or polymethylene groups or by phenylene groups.

The buffer layer may also be selected from the class of silicone materials, based on the combination of silicone polymers and tackifying resins, as described in, for example, "Silicone Pressure Sensitive Adhesives," Handbook of Pressure Sensitive Adhesive Technology, 3rd Edition, pp. 508-517. Silicone pressure sensitive adhesives are known for their hydrophobicity, their ability to withstand high temperatures, and their ability to bond to a variety of dissimilar surfaces.

Some suitable compositions may be described in PCT Patent Application Publication No. WO 00/68336. Other suitable compositions may be based on the family of silicone-polyurea based pressure sensitive adhesives. Such compositions are described in U.S. Pat. No. 5,461,134; U.S. Pat. No. 6,007,914; PCT Patent Application Publication No. WO 96/35458; PCT Patent Application Publication No. WO 96/34028; and PCT Patent Application Publication No. WO 96/34029. Such pressure sensitive adhesives are based on the combination of silicone-polyurea polymers and tackifying agents. Tackifying agents can be chosen from within the categories of functional (reactive) and nonfunctional tackifiers as desired. The level of tackifying agent or agents can be varied as desired so as to impart the desired tackiness to the adhesive composition. For example, in one embodiment, the pressure sensitive adhesive composition may be a tackified polydiorganosiloxane oligurea segmented copolymer including (a) soft polydiorganosiloxane units, hard polyisocyanate residue units, wherein the polyisocyanate residue is the polyisocyanate minus the —NCO groups, optionally, soft and/or hard organic polyamine units, wherein the residues of isocyanate units and amine units are connected by urea linkages; and (b) one or more tackifying agents (e.g., silicate resins, etc.).

In some embodiments, the barrier layer may be, for example, a single or double-sided water-impermeable adhesive tape. In other embodiments, the barrier layer may be, for example, a gasket coated on one or both sides with water-impermeable adhesive. In other embodiments, the barrier layer may be, for example, a water-impermeable laminate material.

Fabrication

The substrate can be fabricated using any convenient method, including, but not limited to, micromolding and casting techniques, embossing methods, surface micro-machining and bulk-micromachining. The latter technique involves formation of microstructures by etching directly into a bulk material, typically using wet chemical etching or reactive ion etching. Surface micro-machining involves fabrication from films deposited on the surface of a substrate.

Although the foregoing discussion has used DNA as a nucleic acid, it would be obvious to a person of reasonable skill in the art to apply the methods disclosed herein to other nucleic acids, including RNA sequences or combinations of RNA and DNA sequences.

It is to be understood that certain descriptions of the present invention have been simplified to illustrate only those elements and limitations that are relevant to a clear understanding of the present invention, while eliminating, for purposes of clarity, other elements. Those of ordinary skills in the art, upon considering the present description of the invention, will recognize that other elements and/or limitations may be desirable in order to implement the present invention. However, because such other elements and/or limitations may be readily ascertained by one of ordinary skill upon considering the present description of the invention, and are not necessary for a complete understanding of the present invention, a discussion of such elements and limitations is not provided herein.

EXAMPLES

The following Example is illustrative of the above invention. One skilled in the art will readily recognize that the techniques and reagents described in the Example suggest many other ways in which the present invention could be practiced.

Example 1

This example illustrates the fabrication of a microarray reactor for the quantitative analysis of nucleic acids using a polymerase chain reaction (PCR) process and an evanescent wave detection technique.

The reaction chamber is made of a glass cover plate and a thermally conductive polypropylene substrate. The interior surface of the glass cover plate is chemically modified to reduce the adsorption of fluorescent substances and other contaminants. The target nucleic acid probes are tethered to the interior surface of the glass cover plate in a known, two-dimensional pattern. The glass cover plate is also transparent and suitable for an evanescent wave detection technique.

The thermally conductive polypropylene substrate with an interior cavity is fabricated using a molding method. An inlet and an outlet are incorporated into the substrate. The glass cover plate and the polypropylene substrate are assembled and sealed together by a buffer layer to form a reactor. After the sample is loaded, both the inlet and the outlet are sealed with a rubber plug.

To prevent liquid leakage of the reactor with thermal cycling, a buffer layer is used between the substrate and the cover plate. A curable silicone rubber (KE3475 from Shin-Etsu Chemical Co., Ltd., Japan) is used as a buffer layer. This silicone rubber is water-impenetrable and able to withstand temperatures between 4° C. through 95° C. This silicone rubber will also not interfere with the PCR process or exhibit low fluorescence after curing. To prevent damage to the glass cover plate, the polypropylene substrate, and the immobilized target probe the silicon rubber is a room temperature vulcanizing (RTV) material.

The sample and various analytical reagents and reactants are introduced into the reaction chamber from an external source through inlet port. The outlet port acts as a blowhole when fluid is introduced in through inlet port. After the sample and various analytical reagents and reactants is added, a set of rubber plugs with the proper size, hardness, and chemical resistance are used to seal the inlet port and outlet port of the reaction chamber.

When using the reactor for nucleic acid detection, the reactor and the reagent inside is heated and cooled down by a PCR temperature cycling program. For example, a semiconductor cooler is used for heating/cooling the substrate made of a thermally conductive polypropylene material. During the PCR process, the target DNA in the chamber is exponential amplified and the amplified DNA products are hybridized to the target probe tethered on the interior surface of the glass cover plate at annealing/extending step in every amplification cycle. The glass cover plate is suitable for fluorescent detection by evanescent wave. The glass cover plate may be made, for example, of K9 optical glass with refractive index larger than the refractive index of the PCR/hybridization buffer inside the reactor. A fluorescent molecule, for example, CY5, may be used for PCR primer labeling. CY5 is excited maximally at 649 nm and emits maximally at 670 nm.

The invention has been described with reference to various specific embodiments and techniques. However, it should be understood that many variations and modifications may be made while remaining within the spirit and scope of the invention.

What is claimed is:

1. A reactor for the quantitative analysis of target nucleic acids, comprising:
    a thermally conductive polypropylene substrate having a first planar opposing surface, and a cavity;
    a buffer layer comprising water-impermeable sealant arranged over and adhered to the first planar opposing surface of the substrate;
    a K9 optical glass cover plate with probes tethered to the interior surface of the cover plate in a known two-dimensional pattern, where the cover plate is arranged over the buffer layer, the cover plate in combination with the cavity, the first planar opposing surface, and buffer layer defining a reaction chamber; and
    at least one inlet port and at least one outlet port communicating with the reaction chamber through the substrate enabling the passage of fluid comprising a sample to be analyzed, analytical reagents, and/or reactants from an external source into and through the reaction chamber, and thereby defining a fluid flow path;
    wherein the reactor is configured for quantitative analysis of target nucleic acids using a polymerase chain reaction (PCR) process and an evanescent wave detection technique where the evanescent wave enters the reaction chamber through the cover plate to which the target nucleic acid probes are tethered.

2. The reactor of claim 1, wherein the substrate, the buffer layer, and the cover plate are each independently comprised of a chemically inert material that is thermally stable and resistant to contamination.

3. The reactor of claim 1, wherein the water-impermeable sealant is a room temperature vulcanizing silicone rubber.

4. A reactor for the quantitative analysis of target nucleic acids, comprising:
    a substrate having a first planar opposing surface the substrate having a cavity;
    a buffer layer comprising water-impermeable sealant arranged over and adhered to the first planar surface of the substrate;
    a K9 optical glass cover plate with probes tethered to the interior surface of the cover plate in a known two-dimensional pattern, where the cover plate is arranged over the buffer layer, the cover plate in combination with the cavity and buffer layer defining a reaction chamber; and
    at least one inlet port and at least one outlet port communicating with the reaction chamber through the substrate enabling the passage of fluid comprising a sample to be analyzed, analytical reagents, and/or reactants from an external source into and through the reaction chamber, and thereby defining a fluid flow path;
    wherein the reactor is configured for quantitative analysis of target nucleic acids by a polymerase chain reaction (PCR) process and an evanescent wave detection technique where the evanescent wave enters the reaction chamber through the cover plate to which the target nucleic acid probes are tethered,
    wherein the substrate is thermally conductive polypropylene that has with a thermal conductivity greater than about 1 W/mK.

5. The reactor of claim 1, wherein the buffer layer is a continuous stripe of water-impermeable sealant around the periphery of the reaction chamber.

6. The reactor of claim 4, wherein the buffer layer is a continuous stripe of water-impermeable sealant around the periphery of the reaction chamber.

* * * * *